United States Patent
Masada et al.

(10) Patent No.: US 8,833,363 B2
(45) Date of Patent: Sep. 16, 2014

(54) EJECTION LIQUID, EJECTION METHOD, METHOD FOR FORMING LIQUID DROPLETS, LIQUID EJECTION CARTRIDGE AND EJECTION APPARATUS

(75) Inventors: Yohei Masada, Tokyo (JP); Masaru Sugita, Toyko (JP); Hideki Kaneko, Yokohama (JP); Takeshi Miyazaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 328 days.

(21) Appl. No.: 12/968,088

(22) Filed: Dec. 14, 2010

(65) Prior Publication Data

US 2011/0079223 A1    Apr. 7, 2011

Related U.S. Application Data

(62) Division of application No. 11/628,452, filed as application No. PCT/JP2005/018070 on Sep. 22, 2005, now abandoned.

(30) Foreign Application Priority Data

Sep. 27, 2004  (JP) .................................. 2004-279864
Aug. 31, 2005  (JP) .................................. 2005-252270

(51) Int. Cl.
| | |
|---|---|
| A61M 11/00 | (2006.01) |
| B41J 2/06 | (2006.01) |
| A61K 38/00 | (2006.01) |
| A61M 15/00 | (2006.01) |
| B41J 2/05 | (2006.01) |
| C12N 5/00 | (2006.01) |
| C11D 10/00 | (2006.01) |

(52) U.S. Cl.
USPC ............ 128/200.14; 128/203.27; 128/203.26; 128/203.12; 128/204.24; 347/1; 347/20; 347/54; 347/56; 347/63; 347/68; 400/106; 435/395; 514/1.1

(58) Field of Classification Search
None
See application file for complete search history.

(56) References Cited

U.S. PATENT DOCUMENTS 4,292,041 A * 9/1981 Fullerton ........................ 436/71
4,877,745 A * 10/1989 Hayes et al. ................... 436/166
(Continued)

FOREIGN PATENT DOCUMENTS

| EP | 0 919 242 A2 | 6/1999 |
| JP | 11-099000 | 4/1999 |

(Continued)

OTHER PUBLICATIONS

Delaney, Jr. J.T. "Reactive Inkjet Printing & Functional Inks: a Versatile Route to New Programmed Materials" Thesis, Eindhoven University of Technology, Sep. 7, 2010, 159 pp.*

(Continued)

*Primary Examiner* — Jon P Weber
*Assistant Examiner* — Aaron J Kosar
(74) *Attorney, Agent, or Firm* — Fitzpatrick, Cella, Harper and Scinto

(57) ABSTRACT

An ejection liquid capable of being stably ejected based on a system using thermal energy even if the liquid contains at least one selected from the group consisting of proteins and peptides, and a method and an apparatus for ejecting the liquid containing at least one selected from the group consisting of proteins and peptides using this system are provided. The applicability of the liquid for use in an inkjet system using thermal energy is improved by adding at least one selected from the group consisting of amino acids and salts thereof and a surfactant to an aqueous solution containing at least one selected from the group consisting of proteins and peptides.

8 Claims, 7 Drawing Sheets

(56) References Cited

U.S. PATENT DOCUMENTS

Figure 1:
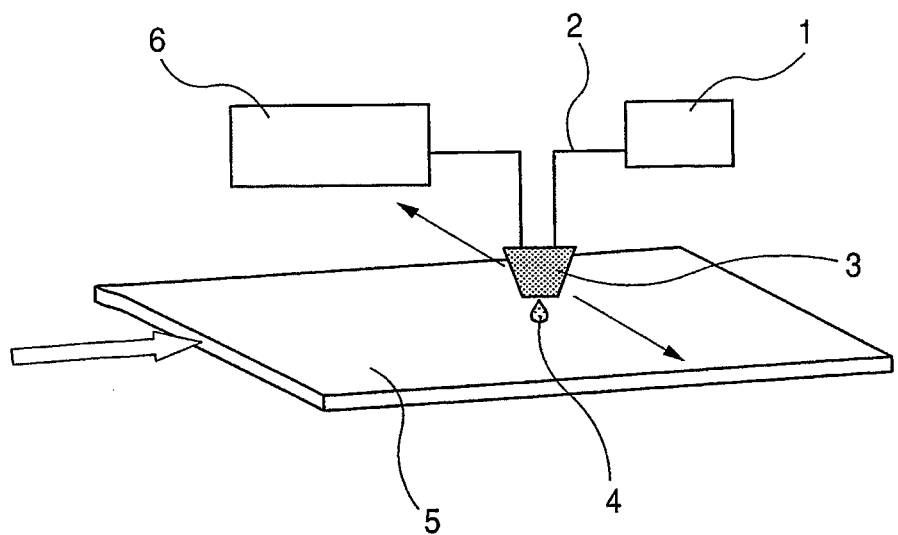

| | | | |
|---|---|---|---|
| 5,223,408 A * | 6/1993 | Goeddel et al. | 435/69.3 |
| 5,223,440 A | 6/1993 | Teng et al. | |
| 5,300,958 A * | 4/1994 | Burke et al. | 347/28 |
| 5,338,688 A * | 8/1994 | Deeg et al. | 436/180 |
| 5,341,160 A | 8/1994 | Winslow et al. | 347/86 |
| 5,350,616 A * | 9/1994 | Pan et al. | 428/131 |
| 5,370,842 A | 12/1994 | Miyazaki et al. | |
| 5,380,490 A | 1/1995 | Hoshi et al. | |
| 5,426,458 A * | 6/1995 | Wenzel et al. | 347/45 |
| 5,434,606 A * | 7/1995 | Hindagolla et al. | 347/45 |
| 5,449,754 A * | 9/1995 | Nishioka | 506/18 |
| 5,474,796 A * | 12/1995 | Brennan | 427/2.13 |
| 5,477,255 A * | 12/1995 | Huth | 347/87 |
| 5,512,446 A | 4/1996 | Miyazaki et al. | |
| 5,534,441 A | 7/1996 | Miyazaki et al. | |
| 5,595,785 A * | 1/1997 | Hindagolla et al. | 430/320 |
| 5,601,983 A | 2/1997 | Takayama et al. | |
| 5,624,798 A | 4/1997 | Yamamoto et al. | |
| 5,635,966 A * | 6/1997 | Keefe et al. | 347/43 |
| 5,635,968 A * | 6/1997 | Bhaskar et al. | 347/59 |
| 5,636,441 A * | 6/1997 | Meyer et al. | 29/890.1 |
| 5,642,142 A * | 6/1997 | Bohorquez | 347/15 |
| 5,658,802 A * | 8/1997 | Hayes et al. | 436/518 |
| 5,670,315 A | 9/1997 | Yamamoto et al. | |
| 5,677,577 A * | 10/1997 | Barbehenn et al. | 307/98 |
| 5,679,516 A | 10/1997 | Okamoto et al. | |
| 5,679,581 A | 10/1997 | Miyazaki et al. | |
| 5,682,188 A * | 10/1997 | Meyer et al. | 347/61 |
| 5,700,637 A * | 12/1997 | Southern | 435/6.12 |
| 5,700,647 A | 12/1997 | Miyazaki et al. | |
| 5,714,989 A * | 2/1998 | Wade | 347/14 |
| 5,726,690 A * | 3/1998 | Bohorquez et al. | 347/15 |
| 5,736,995 A * | 4/1998 | Bohorquez et al. | 347/14 |
| 5,736,998 A * | 4/1998 | Caren et al. | 347/45 |
| 5,745,128 A * | 4/1998 | Lam et al. | 346/140.1 |
| 5,772,829 A * | 6/1998 | Cowger | 156/291 |
| 5,846,730 A | 12/1998 | Miyazaki et al. | |
| 5,894,841 A | 4/1999 | Voges | |
| 5,958,869 A * | 9/1999 | Noguchi et al. | 510/490 |
| 6,022,961 A | 2/2000 | Yamamoto et al. | |
| 6,120,761 A | 9/2000 | Yamazaki et al. | |
| 6,221,653 B1 * | 4/2001 | Caren et al. | 435/287.2 |
| 6,267,985 B1 | 7/2001 | Chen et al. | |
| 6,300,079 B1 * | 10/2001 | Imajo et al. | 435/7.1 |
| 6,525,102 B1 | 2/2003 | Chen et al. | |
| 6,926,392 B2 | 8/2005 | Sasaki et al. | |
| 7,030,086 B2 | 4/2006 | Chen et al. | |
| 7,605,124 B2 * | 10/2009 | Masada et al. | 514/1.1 |
| 7,659,987 B2 | 2/2010 | Utsunomiya et al. | |
| 7,827,982 B2 * | 11/2010 | Masada et al. | 128/200.14 |
| 2002/0092519 A1 | 7/2002 | Davis | |
| 2002/0177221 A1 | 11/2002 | Nishiguchi et al. | |
| 2002/0182721 A1 | 12/2002 | Nishiguchi et al. | |
| 2003/0078384 A1 | 4/2003 | Levy et al. | |
| 2003/0119179 A1 | 6/2003 | Okamoto et al. | |
| 2003/0190316 A1 | 10/2003 | Kakuta et al. | |
| 2004/0037803 A1 | 2/2004 | Sato | |
| 2004/0259083 A1 | 12/2004 | Oshima | |
| 2006/0246508 A1 | 11/2006 | Watanabe et al. | |
| 2007/0222842 A1 | 9/2007 | Masada et al. | |
| 2007/0259394 A1 | 11/2007 | Kanome et al. | |
| 2008/0029083 A1 | 2/2008 | Masada et al. | |
| 2009/0053174 A1 | 2/2009 | Kaneko et al. | |
| 2009/0060869 A1 | 3/2009 | Sugita et al. | |

FOREIGN PATENT DOCUMENTS

| | | |
|---|---|---|
| JP | 2000-302689 | 10/2000 |
| JP | 2002-248171 | 9/2002 |
| JP | 2002-355025 | 12/2002 |
| JP | 2003-510368 | 3/2003 |
| JP | 2003-154655 | 5/2003 |
| JP | 2004-196824 | 7/2004 |
| SU | 1702317 | 12/1991 |
| WO | 01/24814 | 4/2001 |
| WO | 01/49274 A2 | 7/2001 |
| WO | 02/11695 | 2/2002 |
| WO | 02/13860 | 2/2002 |
| WO | 02/17957 | 3/2002 |
| WO | 02/092813 | 11/2002 |
| WO | 02/094342 | 11/2002 |

OTHER PUBLICATIONS

Kendrick, G.W., et al., "Byproducts of Plasma Fractionation", Blood Program in World War II. 1964, archived online Aug. 13, 2004 <http://history.amedd.army.mil/booksdocs/wwii/blood/chapter13.htm>, pp. 359-369.

Ghadimi, H. and Pecora, P. "Free Amino Acids of Different Kinds in Milk" Am. J. Clin. Nutr., 1963, 13 (2), pp. 75-81.

Official Action dated Mar. 26, 2008 in Japanese Application No. 2005-252270, 4 pages.

Kitoku Kudo, et al., "Control for inhibition and encourage of aggregation by addition of small molecule", Summary of Lecture in Annual Meeting of Japan Society for Bioscience, Biotechnology, and Agrochemistry, vol. 2002, 2002, pp. 216.

Kentaro Shiraki, Small molecule additive for inhibiting deactivation and aggregation of protein, Seibutsu Butsuri (Biophys), vol. 44, No. 2, 2004, pp. 87-90.

Leonardo R. Allain, et al., "Microarray sampling-platform fabrication using bubble-jet technology for a biochip system", Fresenius J. Anal. Chem., vol. 371, 2001, pp. 146-150.

E.I. Howard, et al., "Ink-Jet Printer Heads for Ultra-Small-Drop Protein Crystallography", BioTechniques, vol. 33, No. 6, Dec. 2002, pp. 1302-1306.

Indian Office Action dated Apr. 18, 2012 in Indian Application No. 1747/CHENP/2007, 2 pages.

European Search Report dated Oct. 29, 2012 in European Application No. 05787530.4, 9 pages.

Goodall, et al., "Aerosolization of Protein Solutions Using Thermal Inkjet Technology", XP008098212, Journal of Aerosol Medicine, vol. 15, No. 3, 2002, pp. 351-357.

* cited by examiner

EJECTION LIQUID, EJECTION METHOD, METHOD FOR FORMING LIQUID DROPLETS, LIQUID EJECTION CARTRIDGE AND EJECTION APPARATUS

This application is a divisional of U.S. patent application Ser. No. 11/628,452, which was the national stage of International Application No. PCT/JP2005/018070, filed Sep. 22, 2005, the contents both of which are incorporated by reference herein.

TECHNICAL FIELD

The present invention relates to a liquid composition containing at least one type of protein and peptide suitable for forming liquid droplets and a method of forming the liquid droplets, as well as an ejection apparatus using the method of forming the liquid droplets.

BACKGROUND ART

At present, many attempts have been made to use a protein solution in the form of liquid droplets. Such liquid droplets of a protein solution and technique thereof are applied to a drug delivery method via transmucosal administration and to a biochip and a biosensor requiring an extremely small amount of protein. Furthermore, attention is drawn to a method of forming fine liquid droplets of a protein in controlling protein crystals and screening physiologically active substances (see Japanese Patent Application Laid-Open No. 2002-355025, Allain L R et. al. "Fresenius J. Anal. Chem.", 2001, Vol. 371, p. 146-150 and Howard E I, Cachau R E "Biotechniques", 2002, Vol. 33, p. 1302-1306).

Recently, proteins, in particular, enzymes and useful proteins having physiological activities have come to be produced in a large scale by genetic recombination technologies. In these circumstances, a means for forming liquid droplets of a protein may be a useful tool for screening and using novel proteinaceous drugs and developing application fields. Of them, a means for administering various drugs to patients in the form of fine liquid droplets has increased in importance. In particular, a means for administering biological substances including proteins and peptides through the lung becomes important. The lung has lung alveoli whose surface area is as large as 50 to 140 $m^2$ and the epithelium serving as an adsorption barrier, whose thickness is as extremely thin as 0.1 μm, as well as poor enzymatic activity compared to that in the digestive tract. For these reasons, the lung has received attention as a potential administration route in place of an injection route for macromolecular peptide based drugs represented by insulin.

Generally, it is known that the deposition of fine liquid droplets of a drug within the lung varies depending upon the mass median aerodynamic diameter. Of the lung alveoli, to deliver liquid droplets to the lung alveoli present deepest within the lung, liquid droplets having a narrow particle size distribution within 1 to 5 μm must be administered with high reproducibility. Therefore, development of an administration form enabling such an administration and a stable drug preparation are required.

There are some conventional methods for administering a drug preparation within the body, especially, around the respiratory organs. These methods will be described below.

In a metered dose inhaler (MDI) for administering a suspension in aerosol form by using a liquefied non-inflammable gas or flame-retardant gas as a propellant, since the unit volume, that is, the volume of the liquefied gas supplied in a single spray operation time, is regulated, a constant amount of liquid droplets can be sprayed. However, problems still remain unsolved in controlling the size of liquid droplets by regulating the unit volume of the liquefied gas. In addition, it is difficult to say that the propellant is good for health.

In a spray method for a liquid agent containing water or ethanol as a medium, the liquid agent is converted into fine liquid droplets by ejecting it together with a pressurized carrier gas through a capillary. Therefore, it is theoretically possible to control the spray amount of liquid droplets by regulating the amount of the liquid agent to be supplied to the capillary channel. However, it is still difficult to control the size of droplets.

In particular, in the spray method, the pressurized gas used for converting a liquid agent into fine liquid droplets is also used as a gaseous carrier (airflow) for transferring the sprayed fine liquid droplets. Therefore, it is structurally difficult to change an amount of fine liquid droplets (density) floating in the carrier-gas airflow in accordance with intended use.

A method for forming liquid droplets having a narrow particle size-distribution is reported in documents (U.S. Pat. No. 5,894,841 and Japanese Patent Application Laid-Open No. 2002-248171). In this method, extremely fine liquid droplets are formed by a liquid droplet generator based on the liquid ejection principle used in inkjet printing and used. In the liquid ejection in accordance with the inkjet system, an ejection liquid is guided into a small chamber and then physical force is applied to the liquid, thereby pushing the liquid from orifices in the form of liquid droplets. When the liquid is pushed by a thermal transducer such as a thin-film resistor through orifices (ejection ports) formed at the top of the chamber, air bubbles are generated (bubble-jet system and a thermal ink-jet system). The liquid may be pushed by use of a piezo vibrator directly through orifices at the top of a chamber (called piezo inkjet system). The liquid introduction chamber and orifices are integrated into a print head device, which is further connected not only to a liquid supply source but also to a controller for controlling ejection of liquid droplets.

To allow the lung to absorb a drug, in particular, a protein/peptide preparation, it is necessary to accurately control a dose of the drug. In view of this, it is very preferable to form liquid droplets based on the principle of the inkjet system, since the ejection amount can be controlled. In this system, although it is desired to eject a liquid without fails, a protein/peptide solution adjusted only in surface tension and viscosity is not ejected stably and difficult to eject with high reproducibility and efficiency in some cases.

DISCLOSURE OF THE INVENTION

An object of the present invention is to provide an ejection liquid (liquid composition) for stably being ejected to form liquid droplets containing at least one selected from the group consisting of proteins and peptides based on an inkjet system using thermal energy, and a method and apparatus suitable for ejecting the ejection liquid.

According to the present invention, there is provided an ejection liquid for use in a system of ejecting the ejection liquid from an ejection port by use of thermal energy, characterized by comprising at least one selected from the group consisting of proteins and peptides, at least one selected from the group consisting of amino acids and salts thereof, and a surfactant in a liquid medium containing water as a main component.

According to the present invention, there is provided a method of ejecting the ejection liquid based on the principle of an inkjet system.

According to the present invention, there is provided a liquid ejection cartridge characterized by comprising a tank storing the ejection liquid and an ejection head based on the principle of a thermal inkjet system.

According to the present invention, there is provided a method of forming liquid droplets of an ejection liquid containing at least one selected from the group consisting of proteins and peptides by applying thermal energy to the liquid, characterized in that the method comprises a step of applying the thermal energy to the liquid with which a channel is filled and thereby ejecting the liquid in the form of liquid droplets from an ejection port communicated with the channel, and the liquid is the aforementioned ejection liquid.

According to the present invention, an ejection liquid for use in attaining stable ejection based on a system of ejecting a liquid from an ejection port by application of thermal energy can be obtained by adding amino acids and a surfactant to a solution containing at least one selected from the group consisting of protein and peptides. The ejection liquid, if it contains a drug component as at least one selected from the group consisting of proteins and peptides, is ejected from a portable ejection apparatus to form liquid droplets and allowed a user to inhale them. In this manner, the drug component, which is at least one selected from the group consisting of proteins and peptides, can reach the lung and then absorbed by the lung. Furthermore, a biochip and a biosensor can be prepared by ejecting liquid droplets by the method on a substrate, and used for sensing and screening biological substances.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 1 is a schematic illustration for showing a method of ejecting a protein onto a substrate;

FIG. 2 is a pattern of protein liquid droplets arranged on a substrate;

FIG. 3 is a schematic illustration of a head cartridge unit of an inhaler;

FIG. 4 is a perspective view of the inhaler;

FIG. 5 is a perspective view of the inhaler of FIG. 4 with an access cover opened;

FIG. 6 is a graph showing an ejection amount when an albumin solution is ejected in accordance with a bubble-jet system;

FIG. 7 is a graph showing rat's blood glucose level with time when insulin is administered;

FIG. 8 is a graph showing an ejection amount when an insulin solution is ejected by a bubble-jet system; and FIG. 9 is a model showing an experimental method of Example.

BEST MODE FOR CARRYING OUT THE INVENTION

Preferred embodiments of the present invention will now be described in detail in accordance with the accompanying drawings.

Now, the present invention will be explained in detail. The protein used in the present invention means a polypeptide composed of numerous amino acids bonded via a peptide bond and capable of dissolving or dispersing in an aqueous solution. The peptide used in the present invention is composed of 50 or less (both inclusive) amino acids bonded via a peptide bond. The protein/peptide may be chemically synthesized or purified from natural sources; however, typically a recombinant of a natural protein/peptide. Usually, a protein/peptide is chemically modified by covalently binding an amino acid residue to a molecule of the protein/peptide. By virtue of such modification, therapeutic effect of the protein/peptide can be prolonged and improved.

In carrying out the present invention, use may be made of various types of proteins and peptides desirably formed into liquid droplets. The proteins and peptides that may be used in the present invention are not particularly limited as long as they have physiological activities to the living body and act within the living body. Most typically, formation of a protein/peptide according to the present invention into liquid droplets is suitable for delivering a therapeutically useful protein/peptide to the lung.

Examples of such a protein/peptide include hemopoietic factors such as calcitonin, a blood coagulation factor, cyclosporine, G-CSF, GM-CSF, SCF, EPO, GM-MSF, and CSF-1; interleukins such as IL-1, IL-2, IL-3, IL-4, IL-5, IL-6, IL-7, IL-8, IL-9, IL-10, IL-11, and IL-12; IGFs; and cytokines including M-CSF, thymosin, TNF and LIF. Furthermore, examples of other available therapeutically effective peptides include vasoactive peptides, interferons such as α-, β-, γ- or common interferon), growth factors or hormones such as human growth hormone or other animal growth hormones (e.g., bovine, hog, and avian growth factors and others), insulin, oxytocin, angiotensin, methionine enkephalin, substance P, ET-1, FGF, KGF, EGF, IGF, PDGF, LHRH, GHRH, FSH, DDAVP, PTH, vasopressin, glucagon, and somatostatin. Use may be made of protease inhibitors such as leupeptin, pepstatin, and metallo proteinase inhibitors (e.g., TIMP-1, TIMP-2 and other proteinase inhibitors); nerve growth factors such as BDNF and NT3; plasminogen activating factors such as tPA, urokinase, and streptokinase; and a partial peptide fragment of a protein having a whole or part of a parent-protein main structure and having at least a part of biological features of the parent protein. Also use may be made of analogues formed by substitution or deletion, or modified amino acids such as peptide analogues, the aforementioned substances modified with water-soluble polymers such as PEG and PVA. It has been clarified that the aforementioned proteins/peptides can be delivered to the lung in the document (Critical Reviews in Therapeutic Drug Carrier Systems, 12(2&3) (1995)).

Furthermore, examples of a substance for use in preparation of a biochip and a biosensor and in screening of a protein/peptide include the aforementioned proteins and peptides, and further include enzymes such as oxidase, reductase, transferase, hydrase, lyase, isomerase, synthetase, epimerase, mutase and racemase; antibodies such as IgG and IgE, receptors and antigens thereof; and proteins/peptides for use in diagnosis such as allergen, chaperone, avidin and biotin, the aforementioned substances being modified with an immobilization reagent.

The protein/peptide to be contained in an ejection liquid may have a molecular weight within the range of 0.3 k to 150 kDa. The content of at least one type of protein/peptide selected from the aforementioned examples in the ejection liquid varies depending upon the intended use and the types of protein/peptide, preferably selected from the range of 1 μg/ml to 200 mg/ml, and more preferably 0.1 mg/ml to 60 mg/ml.

It is known that the ejection performance of ink in accordance with an inkjet system can be generally improved by adding a surfactant and a solvent such as ethylene glycol.

However, when a solution containing at least one type of protein/peptide was ejected, the ejection performance was not improved by simply adding them. Thus, a new additive was required.

According to the studies of the present inventors, it was confirmed that when a liquid containing a protein/peptide in a concentration sufficient to exhibit effective physiological activity and no additives is ejected in accordance with a thermal inkjet system, the liquid is not substantially ejected at an ejection frequency of 20 kHz if the molecular weight is 3000 or more, although the ejection state varies depending upon the type of protein/peptide.

When the thermal inkjet system was applied to the present invention, the best ejection performance was obtained. Therefore, the constitution will be described based on the principle of the thermal inkjet system below.

When the thermal inkjet system is used, it is possible to increase the aperture of an ejection port, increase the heat quantity of thermal pulse used for ejection, improve the size accuracy of a microheater or the like used for ejection and improve reproducibility. Accordingly, liquid droplets of a narrow size distribution can be attained in all of the numerous liquid ejection units arranged at a high density on the head. Since the head can be prepared at low cost, it can be efficiently applied to a small apparatus whose head must be frequently replaced. Hence, when portability and convenience are required, a liquid ejection apparatus of the thermal inkjet system is preferable.

In the inkjet system, a liquid is formed into liquid droplets and sprayed. The controllability of the inkjet system is advantageously high even if an extremely trace amount of liquid is used. As the system of spraying an extremely fine liquid droplets in accordance with the inkjet system, a vibration system using a piezoelectric device and a thermal inkjet system using a micro-heater device are known.

In the vibration system using a piezoelectric device, the miniaturization degree of the piezoelectric device to be employed is limited, so that the number of ejection ports arranged per unit area is limited. As the number of ejection ports to be arranged per unit area increases, the cost of manufacturing the ports greatly increases. In contrast, in the thermal inkjet system, the micro-heater device to be used is relatively easy miniaturized, with the result that the number of ejection ports to be arranged per unit area can be increased and the cost of manufacturing the ports can be significantly reduced, compared to the vibration system employing the piezoelectric device.

In the case of applying the thermal inkjet system, it is necessary to control the physical properties of the liquid to be ejected in order to appropriately control the spray state and liquid amount of micro liquid droplets to be ejected from individual ejection ports. More specifically, in order to obtain fine liquid droplets of a desirable amount, the composition of a liquid constituting the liquid sample to be ejected is investigated in consideration of the type and composition of a solvent and the concentration of a solute.

Furthermore, various technical developments for the ejection mechanisms of liquid droplets have been made based on the principle of the thermal inkjet system. The present invention can be suitably applied to the liquid ejection mechanisms. In a general inkjet head to be installed in a printer, the liquid amount of each of the liquid droplets ejected is only about several picoliters. In contrast, an ejection mechanism and method for obtaining extremely fine liquid droplets each containing a liquid in the order of sub-picoliters or femtoliters have been developed (Japanese Patent Application Laid-Open No. 2003-154655).

When a drug is applied to a subject of a several-µm somatic cell, the drug may be sprayed in the form of the aforementioned extremely fine liquid droplets.

When Liquid droplets of a protein/peptide are formed based on the principle of the inkjet system, fragile configuration of the protein/peptide has a problem. To explain more specifically, when the configuration is destroyed, the protein/peptide is aggregated and decomposed, possibly affecting a proper ejection operation.

Physical force applied when liquid droplets are formed based on the principle of the inkjet system, for example, pressure, sheering force and high surface energy inherent to fine liquid droplets, renders the configurations of many proteins and peptides unstable (when the bubble-jet system and thermal inkjet system are used, heat is added other than the aforementioned forces).

In particular, when liquid droplets are formed by use of the inkjet system, not only long-term storage stability of an ejection liquid itself but also the resistance against various types of loads as mentioned above and stability are required. To be more specifically, the physical action mentioned above is extremely larger than the shearing force and thermal energy applied by general stirring operation and heat treatment (for example, in the case of the thermal inkjet system, a load of 90 atmospheric pressure is conceivably applied momently at about 300° C.). Furthermore, since a plurality of physical forces are applied simultaneously, the stability of a protein tends to decrease much easily than the case where a protein is treated under general conditions. Therefore, conventional stabilization techniques alone are not sufficient to keep the stability. When such a problem occurs, the protein/peptide is aggregated, clogging a nozzle. Thus, it becomes difficult to eject liquid droplets.

Furthermore, since liquid droplets of 1 to 5 µm in size, suitable for inhalation by the lung, are very small compared to the size (16 µm) of general liquid droplets of a presently commercially available printer, the liquid droplets would receive larger surface energy and shearing force. Therefore, it is very difficult to eject the fine liquid droplets of a protein/peptide suitable for inhalation by the lung.

On the other hand, as a method of stabilizing a protein/peptide, it is known that a surfactant, glycerol, various saccharides, water-soluble polyethylene glycol, and albumin are added. Furthermore, it is known that the long-term storage stability of a proteinaceous preparation is attained by a method of adding an amino acid to erythropoietin, G-CSF, and interferon (Japanese Patent No. 03618633, WO 02/017957, and National Publication of International Patent Application No. 2003-510368). However, according to the studies of the present inventors, depending upon the types and concentrations of a protein/peptide and concentration of additive(s), it is impossible to eject liquid droplets in accordance with the thermal inkjet system.

Furthermore, it is known to add additives suitably used in ink for inkjet printing, more specifically, polyols, such as ethylene glycol and glycerol and a humectant (e.g. urea). However, according to the studies of the present inventors, even if these additives are added, they have little effect upon improving ejection performance of a protein/peptide.

As it is known (WO 02/094342), a compound for controlling surface tension and a humectant are added to a liquid composition of a protein/peptide for forming liquid droplets for inhalation by the lung, in accordance with the thermal inkjet system. In this case, a surfactant and a water-soluble polymer such as polyethylene glycol are added to increase the stability of a protein/peptide of a solution within a liquid droplet, by the surface tension and viscosity of the solution and moisture retention action.

However, no mention is made of ejection stability in the pamphlet of WO 02/094342.

Furthermore, according to the studies of the present inventors, it was found that addition of a surfactant and a water-soluble polymer alone has little effect upon improvement of ejection stability depending upon the types of protein/peptide. When the concentration of a protein/peptide is high, the effect of the additive is insufficient and conversely the additive itself may possibly inhibit the ejection stability.

Furthermore, in many cases, a surfactant alone produces no effect, suggesting that the ejection stability of a protein/peptide solution is not regulated by the surface tension and viscosity or moisturize retention action.

In other words, the methods described in the aforementioned documents are not used as a guideline for ensuring ejection stability when a protein/peptide is ejected in accordance with the thermal inkjet system.

Based on the finding, the present inventors studied a liquid containing a protein/peptide for stable ejection with a view to obtain a guideline for ensuring the ejection stability to attain the present invention.

To use a protein/peptide by ejecting it in accordance with the thermal inkjet system, a method of forming a protein chip is disclosed in U.S. Pat. No. 3,610,231 and WO 02/092813.

However, no description is made of whether or not a protein/peptide is actually ejected stably.

The present inventors intensively conducted studies and found that a solution containing at least one type of protein and peptide as an active ingredient, and supplemented with an amino acid, a salt thereof, and a surfactant can be stably ejected in accordance with the principle of an inkjet system using thermal energy.

Surprisingly, a solution containing a protein/peptide supplemented with an amino acid alone, or a solution containing a protein/peptide supplemented with a surfactant alone produces little effect on ejection stability when ejection is performed in accordance with the inkjet system. Even though these two types of substances each have little effect by itself, if combined, they produce a high synergetic effect. Therefore, a solution containing a protein/peptide can be very stably ejected in accordance with the inkjet system.

The reason why an amino acid and a surfactant, if combined, make a great contribution to ejection stability of a protein/peptide containing solution is not clear but presumed as follows. In a solution to which a surfactant and an amino acid are simultaneously added, no change occurs in the critical micelle concentration and foamability of the surfactant. From this, the amino acid conceivably weakly interacts with the protein/peptide, with the result that the concentration of the amino acid on the surface of the protein/peptide increases. In this state, if a solution containing the protein/peptide is ejected in accordance with the thermal inkjet system, a load is applied to the protein/peptide to expose a hydrophobic portion of the protein/peptide. The amino acid reacts with the exposed hydrophobic portion to suppress the collision between other protein and peptide particles, making aggregation difficult. The effect of the amino acid is sufficient to keep the solution of the protein and peptide as it is but insufficient to stabilize the solution having a load imposed by ejection. Thus, it is considered that the addition of an amino acid alone to a solution of a protein/peptide does not produce any effect.

On the other hand, a surfactant presumably acts on insoluble matters in water (precipitants), which are produced when a hydrophobic portion of a protein/peptide is exposed due to the load during ejection or when water molecules are removed from the protein/peptide, or acts on aggregates, which are produced by interacting the hydrophobic portions, thereby redissolving the precipitants and aggregates in water. However, the surfactant alone cannot suppress aggregation of the protein/peptide or help the protein and peptide to keep water molecules. The redissolution effect of the surfactant is therefore considered too poor to ensure the ejection stability.

As described above, it is presumed that these two different effects work in combination to quickly redissolve the precipitants and aggregates, which are inevitably generated to some extent, in water while preventing a large amount of aggregation production, with the result that the transfer of thermal energy to the solution can be stabilized to stabilize ejection.

In carrying out the present invention, the lower the drive frequency of a thermal inkjet head, the better. The ejection stability differs depending upon the drive frequency because when an ejection liquid is heated by the heater of the thermal inkjet head, a protein/peptide becomes partly insoluble in water, preventing energy from the heater from transferring to the solution. When the drive frequency is low, even if insoluble matters are momently produced, they can be redissolved until next driving operation. In contrast, when the drive frequency is high, the redissolution is insufficiently performed until next driving operation, consequently reducing the ejection stability. Nevertheless, to eject a large amount of solution efficiently, ejection must be performed at a high frequency above a predetermined level. A preferably drive frequency in the present invention falls within the range of 0.1 kHz to 100 kHz, and more preferably 1 kHz to 30 kHz.

The term "amino acid" means a compound having an amino group and a carboxyl group with a carbon atom placed between them. The amino acid of the present invention represents 20 types of amino acids present in proteins and peptides constituting a living body. The amino acids used herein may be either D-form or L-form.

Examples of preferable amino acids include arginine, proline, glycine, glutamine, aspartic acid, valine, threonine, alanine and salts thereof. Of them, what are preferably used are arginine, proline and glycine and salts thereof.

The content of at least one selected from the amino acids and salts thereof in an ejection liquid is selected depending upon the type and content of a protein/peptide, and preferably selected from 10 μg/ml to 2.0 g/ml, and more preferably, 1.0 mg/ml to 200 mg/ml.

The term "surfactant" used in the present invention means a compound having both a polar portion and a non-polar portion in a single molecule, in other words, having a polar portion and a non-polar portion connected via a secondary bond such as an ionic bond. The surfactant not only reduces the surface tension between two non-miscible phases by aligning molecules at the interface but also possesses a feature of forming a micelle. In other words, the surfactant is a compound having these polar and non-polar portions locally at regions distant from each other.

The surfactant that can be used here is not limited and preferably at least one selected from the nonionic surfactants and amino acid surfactants used in, for example, the food and medical fields.

Typical examples of such a surfactant include sorbitan fatty acid esters such as sorbitan monocaprylate, sorbitan monolaurate, sorbitan monopalmitate; N-acyl amino acids, which are a surfactant having an amino acid as a hydrophilic group, such as N-coconut oil fatty acid glycine, N-coconut oil fatty acid glutamate, and N-lauroylglutamic acid; amino acid fatty acid salts; glycerol fatty acid esters such as glycerol monocaprylate, glycerol monomyristate, and glycerol monostearate; polyglycerol fatty acid esters such as decaglyceryl monostearate, decaglyceryl distearate, and decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, and polyoxyethylene sorbitan tristearate; polyoxyethylene sorbitan fatty acid esters such as polyoxyethylene sorbitan tetrastearate and polyoxyethylene sorbitan tetraoleate; polyoxyethylene glycerol fatty acid esters such as polyoxyethylene glyceryl monostearate; polyethylene glycol fatty acid esters such as polyethylene glycol distearate; polyoxyethylene alkyl ethers such as polyoxyethylene lauryl ether, polyoxyethylene polyoxypropylene alkyl ethers such as polyoxyethylene polyoxypropylene glycol ether, polyoxyethylene polyoxypropylene propyl ether, and polyoxyethylene polyoxy propylene cetyl ether; polyoxyethylene alkylphenyl ethers such as polyoxyethylene nonylphenyl ether; hardened polyoxyethylene castor oils such as polyoxyethylene castor oil and hardened polyoxyethylene castor oils (polyoxyethylene hydrogenated castor oil); polyoxyethylene beeswax derivatives such as polyoxyethylene sorbit beeswax; polyoxyethylene lanolin derivatives such as polyoxyethylene lanolin; polyoxyethylene fatty acid amides (having an hydrophilic lipophilic balance (HLB) of 6 to 18) such as polyoxyethylene stearic acid amide; anionic surfactants, for example, alkyl sulfates having an alkyl group with 8 to 18 carbon atoms such as sodium cetyl sulfate, sodium lauryl sulfate, and sodium oleyl sulfate; polyoxy ethylene alkyl ether sulfates having 2 to 4 ethylene oxide adducts per mole in average and an alkyl group with 8 to 18 carbon atoms, such as sodium polyoxy ethylene lauryl sulfate; alkyl benzene sulfonates having an alkyl group with 8 to 18 carbon atoms such as sodium lauryl benzene sulfonate; alkyl sulfosaccinate esters having an alkyl group with 8 to 18 carbon atoms such as sodium lauryl sulfosaccinate; natural surfactants, for example, lecithin; glycerophosphoric lipid; sphingophospholipid such as sphingomyelin; and sucrose fatty acid ester having 8 to 18 carbon atoms. These surfactants may be added singly or in the combination of two or more types to the ejection liquid (liquid composition) of the present invention.

Examples of preferable surfactants include polyoxyethylene sorbitan fatty acid ester. Examples of particularly preferable surfactants include polyoxyethylene (20) sorbitan monolaurate, polyoxyethylene (20) sorbitan monostearate, polyoxyethylene (20) sorbitan tristearate, polyoxyethylene (20) sorbitan monooleate (sold under the trademark TWEEN 80), N-coconut oil fatty acid glycine, N-coconut oil fatty acid glutamate, N-lauroylglycine, N-lauroylglutamic acid, N-lauroylsarcosine, lauramide propylbetaine and an arginine coconut oil fatty acid salt. Examples of the most preferable surfactants include polyoxyethylene (20) sorbitan monolaurate, polyoxyethylene (20) sorbitan monooleate, N-coconut oil fatty acid glycine, N-coconut oil fatty acid glutamate, N-lauroylsarcosine, lauramide propylbetaine and an arginine coconut oil fatty acid salt. Examples of surfactants suitable for adsorption by the lung include polyoxyethylene (20) sorbitan monolaurate and polyoxyethylene (20) sorbitan monooleate.

The concentration of a surfactant to be added varies depending upon the type and content of the coexistent protein/peptide; however, may be selected from critical micelle concentration or more within the range of 1 µg/ml to 1.0 g/ml, and more preferably, from 1.0 mg/ml to 200 mg/ml.

The ratio of protein/peptide:amino acid: surfactant varies depending upon the types of individual components; however, protein/peptide, amino acid/salts thereof and surfactant is preferably added in the ratio of 1:0.1 to 200:0.01 to 100 parts by weight, and more preferably, 1:1 to 20:0.1 to 100 parts by weight.

In the present invention, a protein, an amino acid and a surfactant are preferably mixed homogeneously before ejection, either previously or immediately before the ejection.

In embodiments of the present invention, an antibacterial agent, a disinfectant, and/or an antiseptic agent may be added to eliminate a microbial effect. Examples of such an agent(s) include quaternary ammonium salts such as benzalkonium chloride and benzathonium chloride; phenol derivatives such as phenol, cresol and anisole; benzoic acids such as benzoic acids and paraoxy benzoic acid ester; and sorbic acid.

In the embodiments of the present invention, oil, glycerol, ethanol, urea, cellulose, polyethylene glycol, and alginate may be added to increase the physical stability of the ejection liquid during storage. Also, ascorbic acid, citric acid, cyclodextrin, tocopherol and other antioxidants may be added to increase the chemical stability thereof.

A buffer may be added to adjust the pH of the ejection liquid. Examples of such a buffer include ascorbic acid, citric acid, diluted hydrochloric acid, and diluted sodium hydroxide. Other than these, use may be made of a buffer such as sodium hydrogen phosphate, sodium dihydrogen phosphate, potassium hydrogen phosphate, potassium dihydrogen phosphate, PBS, HEPES, or Tris.

As a tonicity agent for a liquid, aminoethyl sulfonate, potassium chloride, sodium chloride, glycerol and sodium acid carbonate may be added.

When an ejection liquid according to the present invention is used as a spray solution, saccharides such as glucose and sorbitol, sweeteners such as asterperm, and flavoring agents such as menthol may be added as a taste and flavor improvement. Not only hydrophilic compounds but also hydrophobic compounds may be used. Compounds may be used in oily-form.

Furthermore, if necessary, various types of additives such as a surface adjuster, viscosity adjuster, solvent, and humectant suitable for an intended use of the ejection liquid, may be added in appropriate amounts. Specific examples of additives that may be added may include hydrophilic binders, hydrophobic binders, hydrophilic thickeners, hydrophobic thickeners, glycol derivatives, alcohols, and electrolytes. Additives selected from the aforementioned examples may be used singly or in the form of a mixture. The substances that may be used as additives are described as minor components that may be added in preparing therapeutic liquid agents in, for example, the pharmacopoeia of each country. It is preferable to use additives acceptable as medical use or food and cosmetic use.

The proportions of the additives to be added vary depending upon the type of protein/peptide; however, in general, preferably fall within the range of 0.001% to 40% by weight, and more preferably, 0.01% to 20% by weight. The amounts of the additives vary depending upon types, quantities, and combination thereof; however, preferably fall within the range of 0.1 to 200 parts by weight relative to 1 part by weight of the aforementioned protein/peptide from the viewpoint of ejection properties.

When an ejection liquid according to the present invention is used for manufacturing a biochip and a biosensor and for screening a protein/peptide, virtually the same systems as in presently commercially available inkjet printers may be used.

On the other hand, a liquid ejection apparatus according to the present invention has an ejection head based on the principle of a thermal inkjet system, that is, capable of ejecting fine liquid droplets of an ejection liquid in accordance with the thermal inkjet system. The ejection head is preferably constituted of numeral ejection units independently driven. In the apparatus, an electrical connector, which sends a plurality of control signals to individual ejection units for driving them independently is integrate with a wire, which connects the electrical connector to each of the ejection units. In addition, the apparatus has a tank containing an ejection liquid, and a liquid channel for supplying the ejection liquid from the tank to the ejection head in accordance with the principle of the thermal inkjet system. These sections are preferably integrated into a liquid ejection cartridge.

Figure 2:
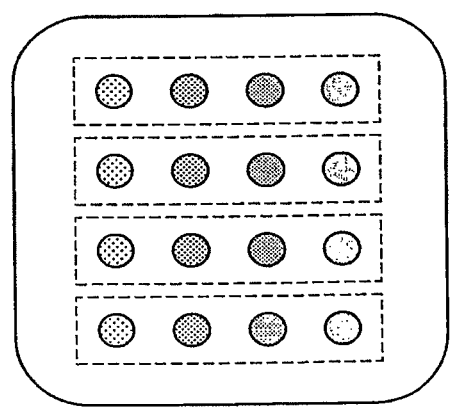

FIG. 1 schematically shows an apparatus for forming protein and peptide spots on a substrate by use of an ejection liquid according to the present invention. A substrate 5 is used as a detection plate having an immobilization region on which a standard substance such as a protein, peptide, enzyme, or antibody is immobilized for detecting various substances contained in a sample. The liquid ejection head 3 at least has a liquid channel (not shown) in which ejection energy is applied to the liquid and an ejection port (not shown) communicated with the channel. When the liquid is supplied from a tank 1 storing the liquid through a channel 2, and ejection energy is applied to the liquid in the channel 2, the liquid is ejected from the ejection port to a predetermined position of the surface of the substrate 5 in the form of a liquid droplet 4. The head 3 is arranged on a carriage capable of moving in the in-plane direction indicated by the arrows. The shooting position of the liquid drop 4 on the substrate 5 can be determined by moving the head 3. The timing of ejecting the liquid drop 4 is controlled by a controller 6 electrically connected to the ejection head 3. FIG. 2 shows a plan view of a pattern of protein/peptide spots arranged on the substrate surface. In the figure, a single type of ejection liquid is used. However, if a plurality of ejection units, each independently driven and ejecting a different ejection liquid, are arranged in the ejection head and connected to predetermined supply systems for the ejection liquids, a plurality of spots different in type can be formed on the substrate. Furthermore, by changing a supply amount of liquid to individual spot formation positions, spots having different deposition amounts can be formed.

At this time, the ejection head 3 may be constituted in various ways depending upon the spot size formed on the substrate and the interval between the spots. When liquid droplets are formed in the order of sub picoliters or femtoliters, use may be made of an ejection head (disclosed in Japanese Patent Application Laid-Open No. 2003-154655) capable of ejecting extremely fine liquid droplets with excellent controllability.

Next, an ejection liquid according to the present invention is applied to a spray apparatus, in particular, an inhaler. Such an inhaler preferably has a section for converting the ejection liquid (liquid agent) into fine liquid droplets and a section in which the sprayed fine liquid droplets are mixed with a gaseous carrier, as discrete members. By virtue of discretely forming the section for converting the ejection liquid into fine liquid droplets and the section for forming airflow containing fine liquid droplets, the amount of a protein/peptide serving as an active ingredient, that is, a predetermined dose per administration thereof, can be added uniformly to the airflow that is inhaled by a subject to be administrated. Furthermore, the ejection head, if it is constituted so as to eject different active ingredients for each of a plurality of ejection units each having a plurality of ejection ports, can control the ejection amounts of a plurality of active ingredients.

By using an ejection head according to the thermal inkjet system having ejection ports densely arranged per unit area as a spray mechanism, the inhaler can be miniaturized such that the user can carry it.

In the inhaler for the lung, it is important that liquid droplets contained in the airflow have a narrow size distribution within the range of 1 to 5 μm. In addition, the inhaler must be miniaturized when the user carries it.

Figure 3:
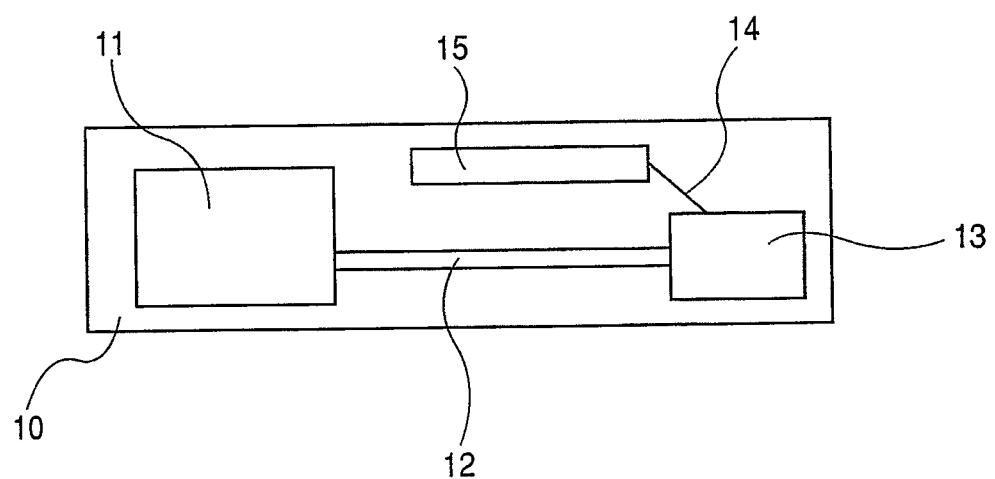

FIG. 3 shows a schematic structure of a liquid ejection section of such an inhaler. The liquid ejection section has a case 10, which accommodates a head section 13, a tank 11 for storing an ejection liquid, a liquid channel 12 for supplying the liquid from the tank 11 to the head section 13, an electrical connection section 15 for interchanging driving signals and control signals with a controller for controlling drive of individual liquid ejection units of the head section 13, and an inner wire 14 connecting the head section 13 and the electrical connection section 15. These parts are integrally formed into one unit structure as a head cartridge unit. The head cartridge unit is detachably (as needed) integrated into the inhaler. The head section 13 suitably has the structure of the liquid droplet ejection head described in Japanese Patent Application Laid-Open No. 2003-154665.

A portable inhaler (inhaler) having a head cartridge unit having such a structure will be explained with reference of FIGS. 4 and 5. The inhaler shown in FIGS. 4 and 5 is an inhaler of medical use reduced in size such that the user can carry it.

Figure 4:
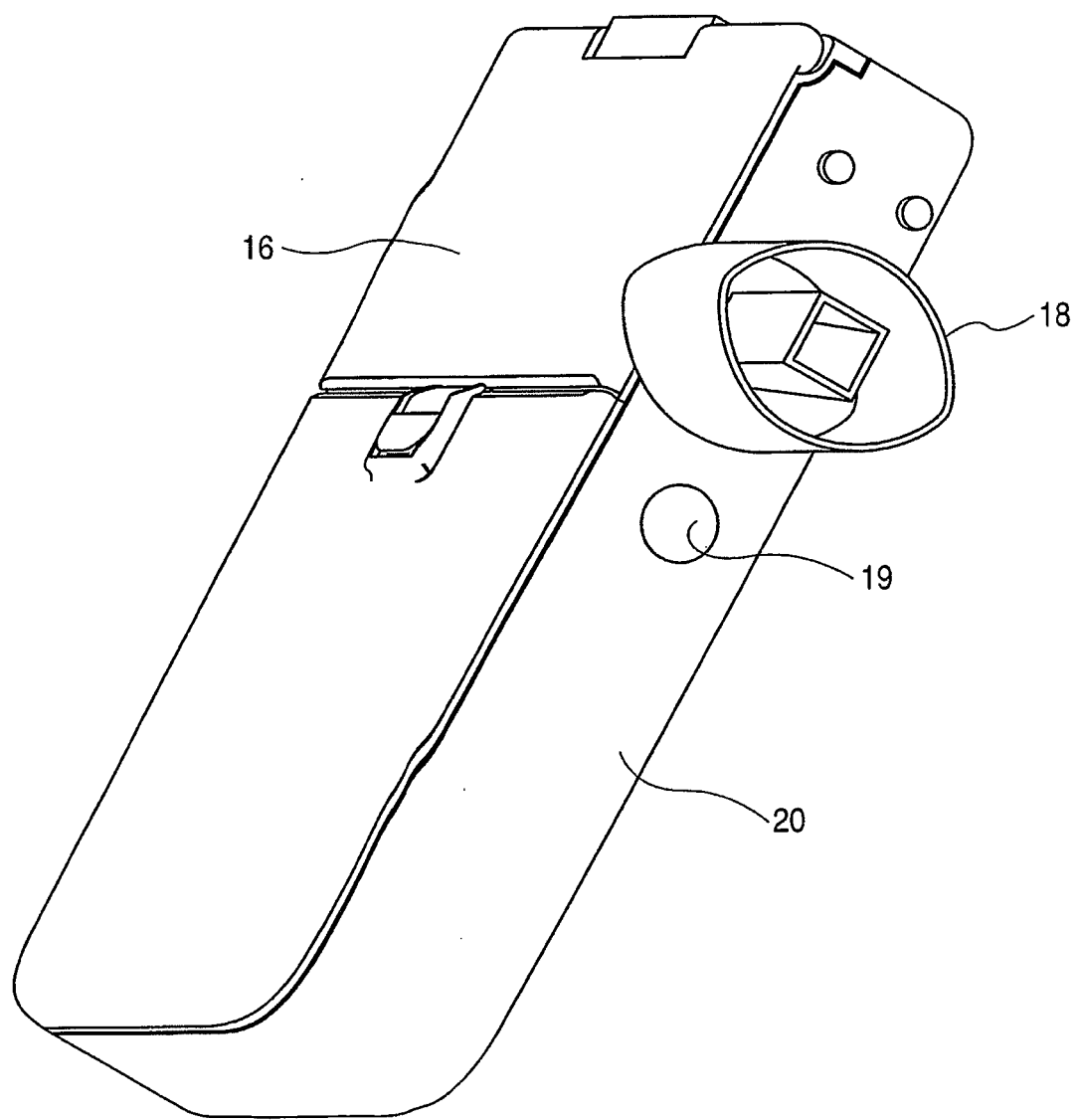

FIG. 4 is a perspective view showing the appearance of the inhaler. A housing is constituted of a main body 20 of the inhaler and an access cover 16. In the housing, a controller and a power source, i.e., battery (not shown) are housed. FIG. 5 shows the state where the access cover 16 is opened. When the access cover 16 is opened, a connecting section between a head cartridge unit 21 and a mouthpiece 18 can be seen. Reference numeral 19 indicates a power-source button. When the user inhales, air is introduced from an air inlet port 17 into the inhaler and guided into the mouthpiece 18, where the air is mixed with liquid droplets ejected from the ejection port provided in the head section 13 of the head cartridge unit 21 to be a mixed airflow, which flows toward the outlet of the mouthpiece 18 designed suitably for holding in user's lips. When the user inserts the top of the mouthpiece into the mouth and breaths while holding it between the teeth, the user can efficiently inhale the liquid droplets ejected from the liquid ejection section of the head cartridge unit.

The head cartridge unit 21 can be detachably (as needed) attached to the inhaler.

Figure 5:
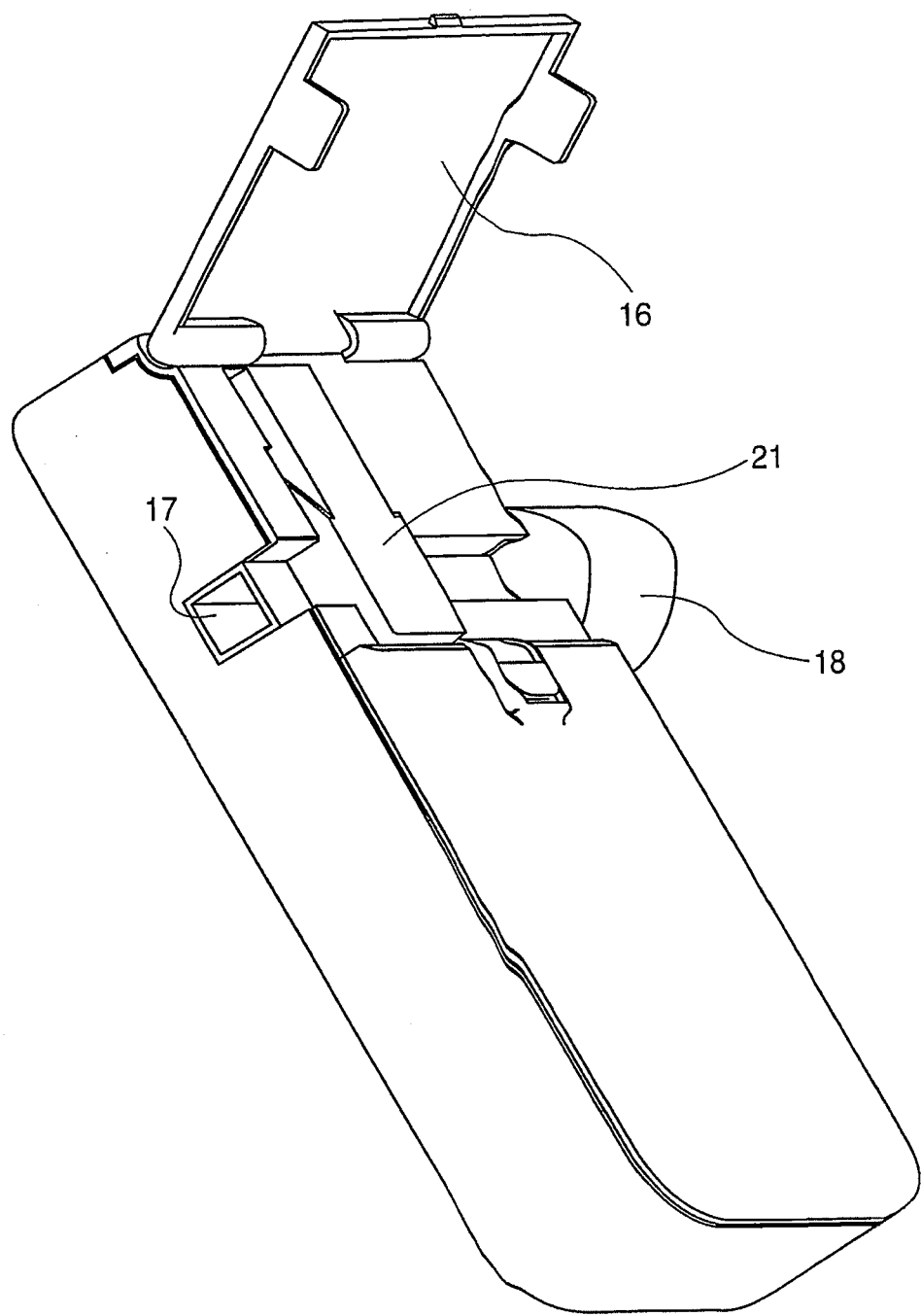

By virtue of the structure shown in FIGS. 4 and 5, the fine liquid droplets are formed and reach the throat and the trachea of the subject (to be administered) naturally with the inspired air. Therefore, the amount of liquid in the formed of sprayed droplets (that is, dose of an active ingredient) can be controlled irrelevant to the volume of inspired air.

EXAMPLES

Reference Example 1

Figure 6:
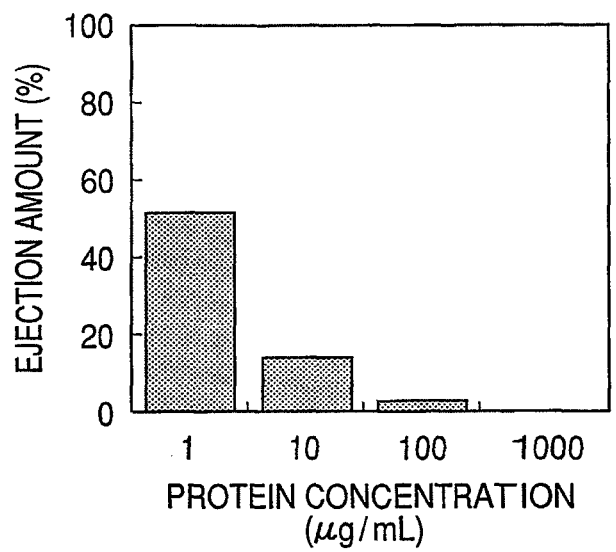

Before describing Examples, an ejection amount when a solution containing a protein alone is ejected in accordance with the thermal inkjet system will be shown in order to facilitate the understanding why it is difficult to eject a protein solution. A solution of albumin in PBS was prepared as the protein solution in various concentrations. Each of the solutions was ejected by a liquid ejection apparatus, which was modified from a bubble-jet printer (trade name: PIXUS 950i manufactured by Canon Inc.) so as to collect the solution. The ejection amount (the amount of a single liquid droplet) of each albumin solution is indicated based on that of pure water (ejected in the same manner) being 100%. The results are shown in FIG. 6.

Ejection is not completely stable even at an albumin concentration as low as 1 μg/mL. It is demonstrated that the ejection amount gradually reduces toward zero as a protein concentration increases. If the ejection amount greatly varies depending upon the protein concentration, the concentration of a protein/peptide in spots cannot be adjusted to a desired one in arranging them on a substrate in the same quantity. Furthermore, when a protein/peptide is contained in an equal amount per dose in applying it as a drug by use of an inhaler, it is difficult to adjust the concentration of the protein/peptide in the ejection liquid. Moreover, when used in an inhaler, liquid droplets must be formed in further smaller sizes by ejection. Ejection of a protein/peptide solution in such a manner is considered difficult.

Now, the present, invention will be described in more detail by way of Examples, which will be provided for facilitating further understanding of the invention and thus should not be construed as limiting the invention. Note that the symbol "%" indicates "% by weight".

Examples 1 to 24 and Comparative Examples 1 to 11

Formation of Liquid Droplets of a Protein Solution Based on the Principle of the Bubble-Jet System An ejection liquid was prepared by dissolving insulin of an appropriate concentration in an aqueous 0.1M HCl solution, adding amino acids and salts thereof and a surfactant while stirring to the solution mixture prepared above, adjusting pH of the mixture to 7.4 with 0.1M NaOH, and adjusting the insulin concentration of the resultant solution with a buffer of pH 7.4 to a predetermined value.

On the other hand, a liquid ejection head having a nozzle of 3 μm in diameter in accordance with the bubble-jet system was prepared. The tank connected to the nozzle was filled with an aqueous solution of 30% ethanol. The ejection head was driven by a controller electrically connected to the liquid ejection head, thereby ejecting the liquid from ejection ports. The resultant liquid droplets (sprayed droplets) was analyzed and confirmed for particle size and particle size distribution by laser diffraction system particle size-distribution measurement apparatus (Sprayteck manufactured by Malvern Inc.). As a result of the analysis, it was found that the liquid droplets had a sharp particle size distribution at the center of about 3 μm.

The ejection liquid prepared in the aforementioned manner was loaded in the tank connected to the liquid ejection head having a nozzle of 3 μm in diameter. Ejection (first ejection) was performed for 1 second, while operating the ejection head by the ejection controller at a frequency of 20 kHz and a voltage of 12V. After the interval of 3 seconds, a second ejection was performed for 1 second. This procedure was repeated 50 times. Whether ejection was performed continuously or not was visually checked. The cases where liquid droplets were ejected continuously even 50 times or more were indicated by reference symbol ○; the cases where ejection of liquid droplets was interrupted in the range of 15 to 50 times were indicated by reference symbol Δ; and the cases where ejection of liquid droplets was interrupted less than 15 times were indicated by reference symbol x. Furthermore, before and after the ejection, the liquid was subjected to HPLC analysis under analysis conditions (apparatus: manufactured by JASCO, Column: YMC-Pack Diol-200, 500×8.0 mm ID, eluant: 0.1 $MKH_2PO_4$—$K_2HPO_4$ (pH7.0) containing 0.2M NaCl, flow rate: 0.7 mL/min, temperature: 25° C., Detection: UV at 215 nm) to confirm the compositional change of the ejection liquid.

As comparative examples, pure water, an insulin solution, an insulin solution containing an amino acid(s) alone, and an insulin solution containing a surfactant alone were prepared and subjected to the same liquid ejection experiment as in Examples.

Note that the formulations and results of Examples and Comparative Examples are shown in Table 1.

TABLE 1

| | Protein | | Amino acid | | Surfactant | | Evaluation of Ejection |
|---|---|---|---|---|---|---|---|
| | Type | Concentration | Type | Concentration | Type | Concentration | performance |
| Example 1 | Insulin | 4 mg/mL | Proline | 2.5 mg/mL | Tween80 | 2.5 mg/mL | ○ |
| Example 2 | Insulin | 4 mg/mL | Arginine | 2.5 mg/mL | Tween80 | 2.5 mg/mL | ○ |
| Example 3 | Insulin | 4 mg/mL | Glycine | 2.5 mg/mL | Tween80 | 2.5 mg/mL | ○ |
| Example 4 | Insulin | 4 mg/mL | Valine | 5.0 mg/mL | Tween80 | 5.0 mg/mL | ○ |
| Example 5 | Insulin | 4 mg/mL | Glutamic acid | 5.0 mg/mL | Tween80 | 5.0 mg/mL | ○ |
| Example 6 | Insulin | 4 mg/mL | Aspartic acid | 5.0 mg/mL | Tween80 | 5.0 mg/mL | ○ |
| Example 7 | Insulin | 4 mg/mL | Threonine | 5.0 mg/mL | Tween80 | 5.0 mg/mL | ○ |
| Example 8 | Insulin | 4 mg/mL | Alanine | 5.0 mg/mL | Tween80 | 5.0 mg/mL | ○ |
| Example 9 | Insulin | 4 mg/mL | Proline | 2.5 mg/mL | N-lauroyl sarcosine | 2.5 mg/mL | ○ |
| Example 10 | Insulin | 4 mg/mL | Arginine | 10 mg/mL | N-lauroyl sarcosine | 0.2 mg/mL | ○ |
| Example 11 | Insulin | 4 mg/mL | Arginine | 2.5 mg/mL | N-lauroyl sarcosine | 2.5 mg/mL | ○ |
| Example 12 | Insulin | 4 mg/mL | Glycine | 2.5 mg/mL | N-lauroyl sarcosine | 2.5 mg/mL | ○ |
| Example 13 | Insulin | 4 mg/mL | Proline | 5.0 mg/mL | N-coconut oil fatty acid glycine | 1.0 mg/mL | ○ |
| Example 14 | Insulin | 4 mg/mL | Arginine | 5.0 mg/mL | N-coconut oil fatty acid glycine | 1.0 mg/mL | ○ |
| Example 15 | Insulin | 4 mg/mL | Glycine | 5.0 mg/mL | N-coconut oil fatty acid glycine | 1.0 mg/mL | ○ |
| Example 16 | Insulin | 4 mg/mL | Proline | 2.5 mg/mL | N-coconut oil fatty acid glutamate | 2.5 mg/mL | ○ |
| Example 17 | Insulin | 4 mg/mL | Arginine | 2.5 mg/mL | N-coconut oil fatty acid glutamate | 2.5 mg/mL | ○ |
| Example 18 | Insulin | 4 mg/mL | Glycine | 2.5 mg/mL | N-coconut oil fatty acid glutamate | 2.5 mg/mL | ○ |
| Example 19 | Insulin | 4 mg/mL | Proline | 2.5 mg/mL | Lauramide propylbetaine | 2.5 mg/mL | ○ |
| Example 20 | Insulin | 4 mg/mL | Arginine | 10 mg/mL | Lauramide propylbetaine | 0.2 mg/mL | ○ |
| Example 21 | Insulin | 4 mg/mL | Glycine | 2.5 mg/mL | Lauramide propylbetaine | 2.5 mg/mL | ○ |
| Example 22 | Insulin | 4 mg/mL | Proline | 2.5 mg/mL | An arginine coconut oil fatty acid salt | 2.5 mg/mL | ○ |
| Example 23 | Insulin | 4 mg/mL | Arginine | 2.5 mg/mL | An arginine coconut oil fatty acid salt | 2.5 mg/mL | ○ |
| Example 24 | Insulin | 4 mg/mL | Glycine | 2.5 mg/mL | An arginine coconut oil fatty acid salt | 2.5 mg/mL | ○ |

TABLE 1-continued

|  | Protein | | Amino acid | | Surfactant | | Evaluation of Ejection performance |
|---|---|---|---|---|---|---|---|
|  | Type | Concentration | Type | Concentration | Type | Concentration |  |
| Comparative Example 1 | Water |  | None | — | None | — | ○ |
| Comparative Example 2 | Insulin | 4 mg/mL | Proline | 10 mg/mL | None | — | x |
| Comparative Example 3 | Insulin | 4 mg/mL | Glycine | 10 mg/mL | None | — | x |
| Comparative Example 4 | Insulin | 4 mg/mL | Glutamic acid | 10 mg/mL | None | — | x |
| Comparative Example 5 | Insulin | 4 mg/mL | Threonine | 10 mg/mL | None | — | x |
| Comparative Example 6 | Insulin | 4 mg/mL | Alanine | 10 mg/mL | None | — | x |
| Comparative Example 7 | Insulin | 4 mg/mL | None | — | Tween80 | 2.5 mg/mL | Δ |
| Comparative Example 8 | Insulin | 4 mg/mL | None | — | N-lauroyl sarcosine | 2.5 mg/mL | Δ |
| Comparative Example 9 | Insulin | 4 mg/mL | None | — | N-coconut oil fatty acid glycine | 2.5 mg/mL | Δ |
| Comparative Example 10 | Insulin | 4 mg/mL | None | — | N-coconut oil fatty acid glutamate | 2.5 mg/mL | Δ |
| Comparative Example 11 | Insulin | 4 mg/mL | None | — | Lauramide propylbetaine | 2.5 mg/mL | Δ |

The pure water of Comparative Example 1, since it contained no insulin, was continuously and stably ejected; however, the pure water containing not only insulin but also an amino acid(s) alone showed no substantial ejection. Furthermore, in the case of the pure water containing not only insulin but also a surfactant alone, the ejection amount was not stable. In contrast, for Examples 1 to 24, ejection was properly performed in a stable ejection state. When the samples of Examples were subjected to HPLC analysis, no difference of a peak in position and intensity was observed before and after ejection. From this, no compositional change was observed. When the sample of Comparative Example 7 was subjected to the HPLC analysis in the same manner, the peak of insulin decreased. From this, it was confirmed that a compositional change occurred.

Example 25

Confirmation of Pharmacological Activity

Figure 7:
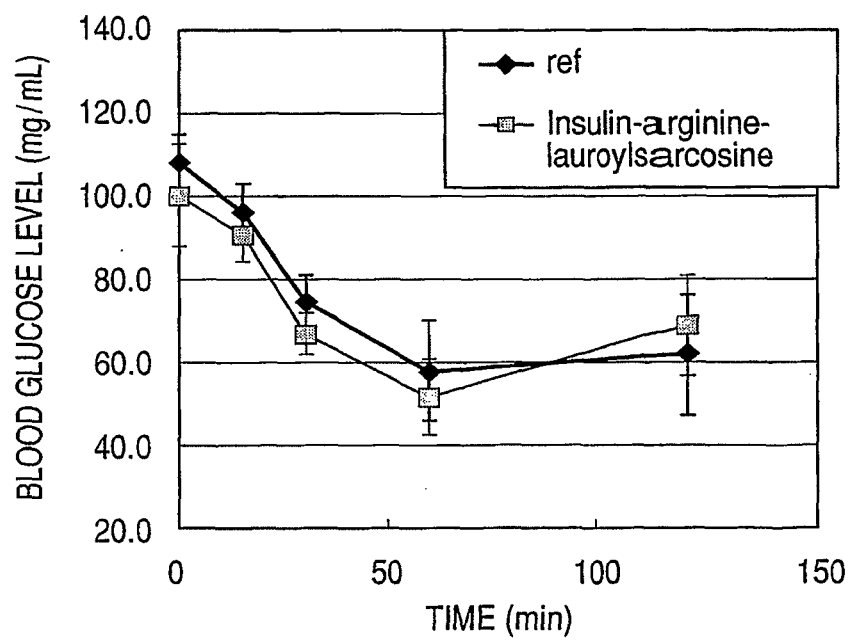

The composition shown in Example 10 was analyzed for pharmacological activity before and after ejection. After anesthetic, Nembutal, was injected to Wister rats (male, 8 week-old, weight: about 250 g) fasted for one day, blood was taken from the tail vein. This is used as a base (control). Thereafter, the solution having the composition of Example 10 was ejected in accordance with the thermal inkjet system. The resultant liquid droplets were collected and subcutaneously injected into the rats in a dose of 1.6 U/kg. Blood was taken from the tail vein 15, 30, 60 and 120 minutes after the injection. The blood samples thus taken were centrifugally separated and the blood glucose levels of the obtained serums were analyzed (one group consisting of 6 rats). The same experiment was performed by using an insulin solution having no additives and not ejected in accordance with the thermal inkjet system as a Comparative Example. The presence and absence of pharmacological activity was analyzed based on a change of the blood glucose level of the rats injected with the liquid droplets of Example 10 (formed by ejection in accordance with the thermal inkjet system). The results are shown in FIG. 7.

As is apparent from the results, the blood glucose level of the rats injected with insulin swiftly decreased. The effect of insulin in reducing a blood glucose level was observed. Also, the effect of the formulation of Example 10 (ejected in accordance with the thermal inkjet system) in reducing blood glucose level was observed. No significant difference in reducing the blood glucose level was observed from the Comparative Example at any measurement point. It was confirmed that the activity was properly maintained after the formulation of Example 10 was ejected in accordance with the inkjet system.

Example 26

Efficiency of Ejection

Solutions containing insulin in a concentration of 1.0 mg/mL with and without an additive(s) were ejected in accordance with the thermal inkjet system. The ejection amount of a solution and its reproducibility were evaluated in the cases where an additive was added and not added to the solution.

Evaluation was performed by using a solution of 1.0 mg/mL insulin containing 1.0 mg/mL proline and 1.0 mg/mL TWEEN 80 (Ins/Pro/Tw);

a solution of 1.0 mg/mL insulin containing 1.0 mg/mL proline (Ins/Pro);

a solution of 1.0 mg/mL insulin containing 1.0 mg/mL TWEEN 80 (Ins/Tw); and a solution of 1.0 mg/mL insulin alone.

Figure 8:
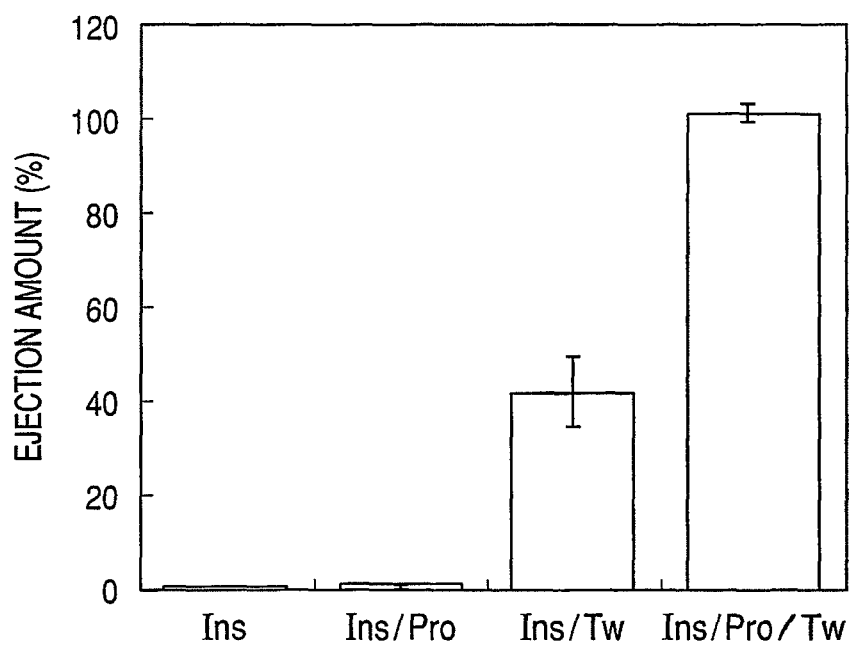

These solutions were ejected by use of a liquid ejection apparatus modified from a bubble-jet printer (trade name: PIXUS950i manufactured by Canon Inc.) so as to collect a liquid. The ejection amount of each solution is plotted on the graph (FIG. 8) based on the ejection amount of pure water ejected in the same manner as above being 100%. The same experiment was repeated 5 times for each solution to obtain average and standard deviation values, which are shown in the graph.

A solution containing insulin alone and a solution containing insulin supplemented with proline show no substantial ejection. The efficiency of ejection is extremely low. The ejection amount of a solution containing insulin supplemented with TWEEN 80 is about 40% relative to that of pure water; however, the ejection amount varies with no reproducibility. On the other hand, the ejection amount of a solution containing insulin supplemented with proline and TWEEN 80 is virtually the same as that of pure water with high reproducibility. The ejection amount of the solution containing insulin supplemented with proline and TWEEN 80 is not less than 100 times as high as that of the solution containing insulin alone and the solution containing insulin supplemented with proline, and about 2.5 times as high as that of the solution containing insulin supplemented with TWEEN 80. Therefore, it is demonstrated that the efficiency in ejection amount of the solution containing insulin supplemented with proline and TWEEN 80 is extremely high.

Examples 27 to 58 and Comparative Examples 12 to 25

Effect on Various Proteins and Concentration of Additives

Subsequently, the solution containing proline+TWEEN 80 and proline+an arginine coconut oil fatty acid salt were selected and added to various types proteins at a predetermined concentration. The ejection solution was prepared by dissolving a protein/peptide of an appropriate concentration in a buffer (pH 7.4), adding amino acids and salts thereof and a surfactant to the resultant solution while stirring, and adjusting the solution with the buffer (pH 7.4) such that the protein/peptide was contained at a predetermined concentration. The ejection solution was subjected to an ejection test in the same manner as in Example 1 to evaluate the ejection performance. Note that the formulations used in the Examples and the results are shown in Table 2 below.

TABLE 2

| | Protein | | Amino acid | | Surfactant | | Evaluation of Ejection performance |
|---|---|---|---|---|---|---|---|
| | Type | Concentration | Type | Concentration | Type | Concentration | |
| Example 27 | Glucagon | 1 mg/mL | Proline | 1.0 mg/mL | Tween80 | 1.0 mg/mL | ○ |
| Example 28 | GLP-1 | 1 mg/mL | Proline | 1.0 mg/mL | Tween80 | 1.0 mg/mL | ○ |
| Example 29 | hGH | 1 mg/mL | Proline | 1.0 mg/mL | Tween80 | 1.0 mg/mL | ○ |
| Example 30 | Erythropoietin | 1 mg/mL | Proline | 2.5 mg/mL | Tween80 | 2.5 mg/mL | ○ |
| Example 31 | IFN α | 1 mg/mL | Proline | 2.5 mg/mL | Tween80 | 2.5 mg/mL | ○ |
| Example 32 | IFN γ | 1 mg/mL | Proline | 2.5 mg/mL | Tween80 | 2.5 mg/mL | ○ |
| Example 33 | Calcitonin | 1 mg/mL | Proline | 2.5 mg/mL | Tween80 | 2.5 mg/mL | ○ |
| Example 34 | γ-globulin | 1 mg/mL | Proline | 2.5 mg/mL | Tween80 | 2.5 mg/mL | ○ |
| Example 35 | Albumin | 1 mg/mL | Proline | 2.5 mg/mL | Tween80 | 2.5 mg/mL | ○ |
| Example 36 | IL-2 | 1 mg/mL | Proline | 2.5 mg/mL | Tween80 | 2.5 mg/mL | ○ |
| Example 37 | IL-6 | 1 mg/mL | Proline | 2.5 mg/mL | Tween80 | 2.5 mg/mL | ○ |
| Example 38 | G-CSF | 1 mg/mL | Proline | 2.5 mg/mL | Tween80 | 2.5 mg/mL | ○ |
| Example 39 | TNFα | 1 mg/mL | Proline | 2.5 mg/mL | Tween80 | 2.5 mg/mL | ○ |
| Example 40 | Antithronbin III | 1 mg/mL | Proline | 2.5 mg/mL | Tween80 | 2.5 mg/mL | ○ |
| Example 41 | LHRH | 1 mg/mL | Proline | 1.0 mg/mL | Tween80 | 1.0 mg/mL | ○ |
| Example 42 | Lysozyme | 5 mg/mL | Proline | 2.5 mg/mL | Tween80 | 2.5 mg/mL | ○ |
| Example 43 | Glucagon | 1 mg/mL | Proline | 0.5 mg/mL | Arginine coconut oil fatty acid salt | 0.5 mg/mL | ○ |
| Example 44 | GLP-1 | 1 mg/mL | Proline | 0.5 mg/mL | Arginine coconut oil fatty acid salt | 0.5 mg/mL | ○ |
| Example 45 | hGH | 1 mg/mL | Proline | 0.5 mg/mL | Arginine coconut oil fatty acid salt | 0.5 mg/mL | ○ |
| Example 46 | Erythropoietin | 1 mg/mL | Proline | 1.0 mg/mL | Arginine coconut oil fatty acid salt | 1.0 mg/mL | ○ |
| Example 47 | IFN α | 1 mg/mL | Proline | 1.0 mg/mL | Arginine coconut oil fatty acid salt | 1.0 mg/mL | ○ |
| Example 48 | IFN γ | 1 mg/mL | Proline | 1.0 mg/mL | Arginine coconut oil fatty acid salt | 1.0 mg/mL | ○ |
| Example 49 | Calcitonin | 1 mg/mL | Proline | 1.0 mg/mL | Arginine coconut oil fatty acid salt | 1.0 mg/mL | ○ |
| Example 50 | γ-globulin | 1 mg/mL | Proline | 1.0 mg/mL | Arginine coconut oil fatty acid salt | 1.0 mg/mL | ○ |
| Example 51 | Albumin | 1 mg/mL | Proline | 1.0 mg/mL | Arginine coconut oil fatty acid salt | 1.0 mg/mL | ○ |
| Example 52 | IL-2 | 1 mg/mL | Proline | 1.0 mg/mL | Arginine coconut oil fatty acid salt | 1.0 mg/mL | ○ |
| Example 53 | IL-6 | 1 mg/mL | Proline | 1.0 mg/mL | Arginine coconut oil fatty acid salt | 1.0 mg/mL | ○ |
| Example 54 | G-CSF | 1 mg/mL | Proline | 1.0 mg/mL | Arginine coconut oil fatty acid salt | 1.0 mg/mL | ○ |
| Example 55 | TNF α | 1 mg/mL | Proline | 1.0 mg/mL | Arginine coconut oil fatty acid salt | 1.0 mg/mL | ○ |
| Example 56 | Antithronbin III | 1 mg/mL | Proline | 1.0 mg/mL | Arginine coconut oil fatty acid salt | 1.0 mg/mL | ○ |
| Example 57 | LHRH | 1 mg/mL | Proline | 0.5 mg/mL | Arginine coconut oil fatty acid salt | 0.5 mg/mL | ○ |
| Example 58 | Lysozyme | 5 mg/mL | Proline | 1.0 mg/mL | Arginine coconut oil fatty acid salt | 1.0 mg/mL | ○ |
| Comparative Example 12 | Glucagon | 1 mg/mL | None | — | None | — | x |
| Comparative Example 13 | GLP-1 | 1 mg/mL | None | — | None | — | x |
| Comparative Example 14 | hGH | 1 mg/mL | None | — | None | — | x |
| Comparative Example 15 | Erythropoietin | 1 mg/mL | None | — | None | — | x |
| Comparative Example 16 | IFN α | 1 mg/mL | None | — | None | — | x |
| Comparative Example 17 | IFN γ | 1 mg/mL | None | — | None | — | x |
| Comparative Example 18 | Calcitonin | 1 mg/mL | None | — | None | — | x |
| Comparative Example 19 | γ-globulin | 1 mg/mL | None | — | None | — | x |
| Comparative | Albumin | 1 mg/mL | None | — | None | — | x |

TABLE 2-continued

|  | Protein | | Amino acid | | Surfactant | | Evaluation of Ejection |
| --- | --- | --- | --- | --- | --- | --- | --- |
|  | Type | Concentration | Type | Concentration | Type | Concentration | performance |
| Example 20 Comparative Example 21 | IL-2 | 1 mg/mL | None | — | None | — | x |
| Comparative Example 22 | IL-6 | 1 mg/mL | None | — | None | — | x |
| Comparative Example 23 | G-CSF | 1 mg/mL | None | — | None | — | x |
| Comparative Example 24 | TNF α | 1 mg/mL | None | — | None | — | x |
| Comparative Example 25 | Antithronbin III | 1 mg/mL | None | — | None | — | x |

In Examples 27 to 58 where a proline and a surfactant were added to 16 types of proteins/peptides, it was confirmed that ejection is properly performed. As is shown in Examples 12 to 25 where no additives were added to these proteins/peptides, virtually or completely no substantial ejection was observed. It was therefore demonstrated that these formulations are effective in stably ejecting the protein/peptide solutions. Furthermore, as a result of HPLC analysis of the solutions of Examples 27 to 58, no change in peak was observed in the chart. It was confirmed that the liquid composition was not changed before and after ejection.

Example 59

Preparation of an Antibody Chip by Use of Inkjet Printer and Sensing Operation

Figure 9:
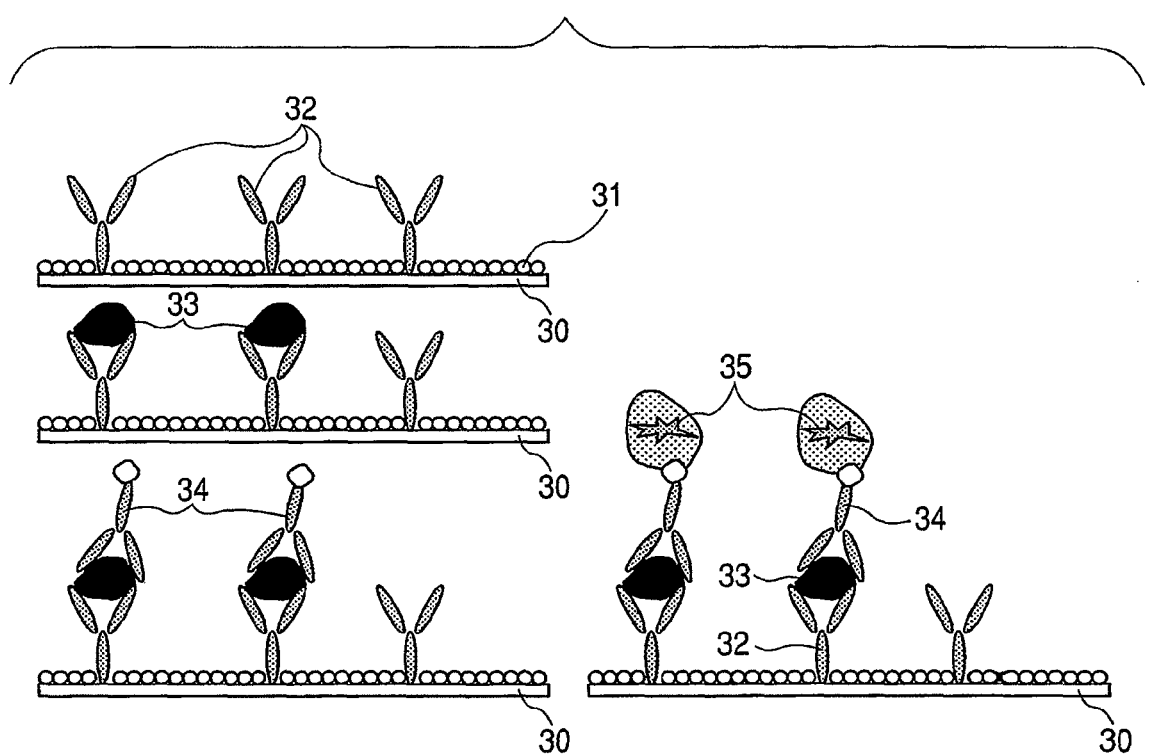

FIG. 9 is a model showing an experimental method of this Example. In the figure, references numerals 30 indicates a substrate, 31 a masking agent, 32 a substance (e.g., protein, peptide) specifically reacting with a test substance, 33 a test substance, 34 a specific substance to the test substance, and 35 a label. This figure schematically shows a series of sensing operations using the antibody chip prepared herein.

The operation will be more specifically explained below. A Human IL2 monoclonal antibody, Human IL4 monoclonal antibody and Human IL6 monoclonal antibody each were prepared in a concentration of 0.1 to 500 μg/mL. Then, proline and TWEEN 80 were added to each antibody solution such than both concentrations became 0.1% (w/w). Each of the ejection liquids thus prepared was loaded in the head of an inkjet printer (trade name: PIXUS950i, manufactured by Canon Inc) and ejected in the form of spots onto a glass plate coated with Poly-L-Lysin in accordance with a predetermined arrange pattern.

The glass plate having liquid spots thereon was incubated at 4° C. and thereafter the (upper) surface of the glass plate was masked by 1% BSA. After the masking, the glass plate was washed well to prepare an antibody chip substrate. Subsequently, solutions containing test substances, recombinants IL2, IL4 and IL6 were prepared in a concentration of 1 μg/mL, and then proline, TWEEN 80 and BSA were added to concentrations of 0.5% (w/w), 0.5% (w/w) and 0.1% (w/w), respectively. Each of the solutions was loaded in the head of an inkjet printer (trade name: PIXUS950i, manufactured by Canon Inc) and ejected onto the antibody-chip substrate in the same pattern as mentioned above. The antibody-chip substrate having the test substance added thereto was covered with a cover glass, and a reaction was performed at 4° C. After completion of the reaction, the antibody-chip substrate was washed well, dried and used as a detection substrate.

Subsequently, labeling was performed to detect the test substance captured on the detection substrate. As a label, a biotin capable of specifically binding to the test substance was used. To antibody solutions containing biotin-labeled Human IL2 monoclonal antibody, biotin-labeled Human IL4 monoclonal antibody, and biotin-labeled Human IL6 monoclonal antibody each in a concentration of 1 μg/mL, proline, TWEEN 80 and BSA were added to final concentrations of 0.5% (w/w), 0.5% (w/w) and 0.1% (w/w), respectively. Thereafter, each of the solutions was loaded in the head of an inkjet printer (trade name: PIXUS950i, manufactured by Canon Inc) and ejected onto the detection substrate in the same pattern. The detection substrate having labeled spots was covered with a cover glass and a reaction was performed at 4° C. After completion of the reaction, the detection substrate was washed well and dried.

To detect the label optically, a solution containing Cy3 labeled streptoavidin in a concentration to 10 μg/mL was prepared. To the solution, proline, TWEEN 80 and BSA were added to final concentrations of 0.5% (w/w), 0.5% (w/w), and 0.1% (w/w), respectively. The solution was loaded in the head of an inkjet printer (trade name: PIXUS950i, manufactured by Canon Inc) and ejected onto the detection substrate in the same pattern as in the above. After completion of the ejection operation, the detection substrate was covered with a cover glass, and a reaction was performed at 4° C. After the reaction, the detection substrate was washed well, dried and thereafter, irradiated with excitation light. The amount (amount of fluorescent signal) of Cy3 emission light was detected by a fluorescent scanner having a filter permeable to wavelength 532 nm. As a result, fluorescent signals varied depending upon types and concentration of samples were detected.

The present invention is not limited to the above embodiments and various changes and modifications can be made within the spirit and scope of the present invention. Therefore to apprise the public of the scope of the present invention, the following claims are made.

This application claims priority from Japanese Patent Application No. 2004-279864 filed Sep. 27, 2004, and Japanese Patent Application No. 2005-252270 filed Aug. 31, 2005 which are hereby incorporated by reference herein.

The invention claimed is:

1. A liquid-ejection method by employing a liquid-ejection device comprising a liquid-ejection head for ejecting a liquid by the thermal inkjet system, a tank for holding a liquid, a liquid-feeding path for supplying the liquid holding in the tank to the liquid-ejection head, the method comprising the step of ejecting the liquid from the ejection head by supplying the liquid holding in the tank to the ejection head through the liquid-feeding path and applying a thermal energy to the liquid supplied by means of driving the liquid-ejection head at drive frequency of the range of 0.1 kHz to 100 kHz, and the liquid comprising:

at least one protein or peptide;

at least one amino acid selected from the group consisting of proline, glycine, glutamic acid, aspartic acid, valine, threonine, alanine, serine, leucine, and isoleucine, or a salt thereof;

a polyoxyethylene sorbitan fatty acid ester; and a liquid medium containing water as a main component.

2. The liquid-ejection method according to claim 1, wherein the at least one protein or peptide is at least one substance selected from the group consisting of calcitonin, insulins, glucagons, interferons, protease inhibitors, cytokines, growth hormones, hemopoietic factors proteins, antibodies and analogs, derivatives and chemically modified substances thereof.

3. The liquid-ejection method according to claim 1, wherein the liquid comprises 0.1 part by weight to 20 parts by weight of the at least one amino acid or a salt thereof and 0.1 part by weight to 10 parts by weight of the surfactant added relative to 1 part by weight of the at least one protein or peptide.

4. The liquid-ejection method according to claim 1, wherein the polyoxyethylene sorbitan fatty acid ester is selected from the group consisting of polyoxyethylene (20) sorbitan monooleate, polyoxyethylene (20) sorbitan monostearate, polyoxyethylene (20) sorbitan tristearate and polyoxyethylene (20) sorbitan monolaurate.

5. A liquid-ejection method by employing a liquid-ejection device comprising a liquid-ejection head for ejecting a liquid by the thermal inkjet system, a tank for holding a liquid, a liquid-feeding path for supplying the liquid holding in the tank to the liquid-ejection head, the method comprising the step of ejecting the liquid from the ejection head by supplying the liquid holding in the tank to the ejection head through the liquid-feeding path and applying a thermal energy to the liquid supplied by means of driving the liquid-ejection head at drive frequency of the range of 0.1 kHz to 100 kHz, and the liquid comprising:

at least one protein or peptide;

at least one amino acid selected from the group consisting of proline, glycine, alanine, valine, leucine, isoleucine or a salt thereof;

at least one surfactant selected from the group consisting of N-lauroylsarcosine, N-acylglycine, N-acylglutamic acid and alkylamide propylbetaine; and a liquid medium containing water as a main component.

6. The liquid-ejection method according to claim 5, wherein the alkylamide propylbetaine is lauramide propylbetaine.

7. The liquid-ejection method according to claim 5, wherein the at least one protein or peptide is at least one substance selected from the group consisting of calcitonin, insulins, glucagons, interferons, protease inhibitors, cytokines, growth hormones, hemopoietic factors proteins, antibodies and analogs, derivatives and chemically modified substances thereof.

8. The liquid-ejection method according to claim 5, wherein the liquid comprises 0.1 part by weight to 20 parts by weight of the at least one amino acid or a salt thereof_and 0.1 part by weight to 10 parts by weight of the surfactant added relative to 1 part by weight of the at least one protein or peptide.

* * * * *